United States Patent [19]

Orr, Jr.

[11] 4,135,388

[45] Jan. 23, 1979

[54] METHOD AND APPARATUS FOR AUTOMATICALLY FRACTIONATING A SAMPLE OF PARTICULATE MATERIAL INTO DISCRETE SIZE FRACTIONS

[75] Inventor: Clyde Orr, Jr., Dunwoody, Ga.

[73] Assignee: Georgia Tech Research Institute, Atlanta, Ga.

[21] Appl. No.: 847,087

[22] Filed: Oct. 31, 1977

[51] Int. Cl.$^2$ .......................................... G01N 15/02
[52] U.S. Cl. .............................. 73/61.4; 73/432 PS; 209/270
[58] Field of Search .................. 73/432 PS, 61.4; 209/270, 284, 285, 286, 288, 289, 290, 303

[56] References Cited

U.S. PATENT DOCUMENTS

| | | | |
|---|---|---|---|
| 2,782,926 | 2/1957 | Saxe | 73/432 PS X |
| 3,439,800 | 4/1969 | Tonjes | 73/432 PS X |
| 3,545,281 | 12/1970 | Johnson | 73/432 PS |
| 3,690,183 | 9/1972 | Livingood | 73/432 PS |
| 3,943,754 | 3/1976 | Orr, Jr. | 73/432 PS X |

FOREIGN PATENT DOCUMENTS 368525  1/1973  U.S.S.R. ................................. 209/270

Primary Examiner—Richard C. Queisser
Assistant Examiner—Joseph W. Roskos
Attorney, Agent, or Firm—Newton, Hopkins & Ormsby

[57] ABSTRACT

A fractionating apparatus under microprocessor control including a tumbler having a series of screens of progressively larger openings around its periphery. A sample of particulate material is passed successively through each of the screens by incremental rotation of the tumbler. To aid in classifying the fractions, a spray of fluid is projected against the screens and a rocking motion is imparted to the tumbler. The smallest fraction, not being retained, is entrained in a moving stream of fluid and passed directly to a porous weighing member. When this entire fraction is deposited and weighed, the next larger fraction is accumulated in the weighing member. These individual weights and their sum are recorded and from them size percentages are computed.

6 Claims, 1 Drawing Figure

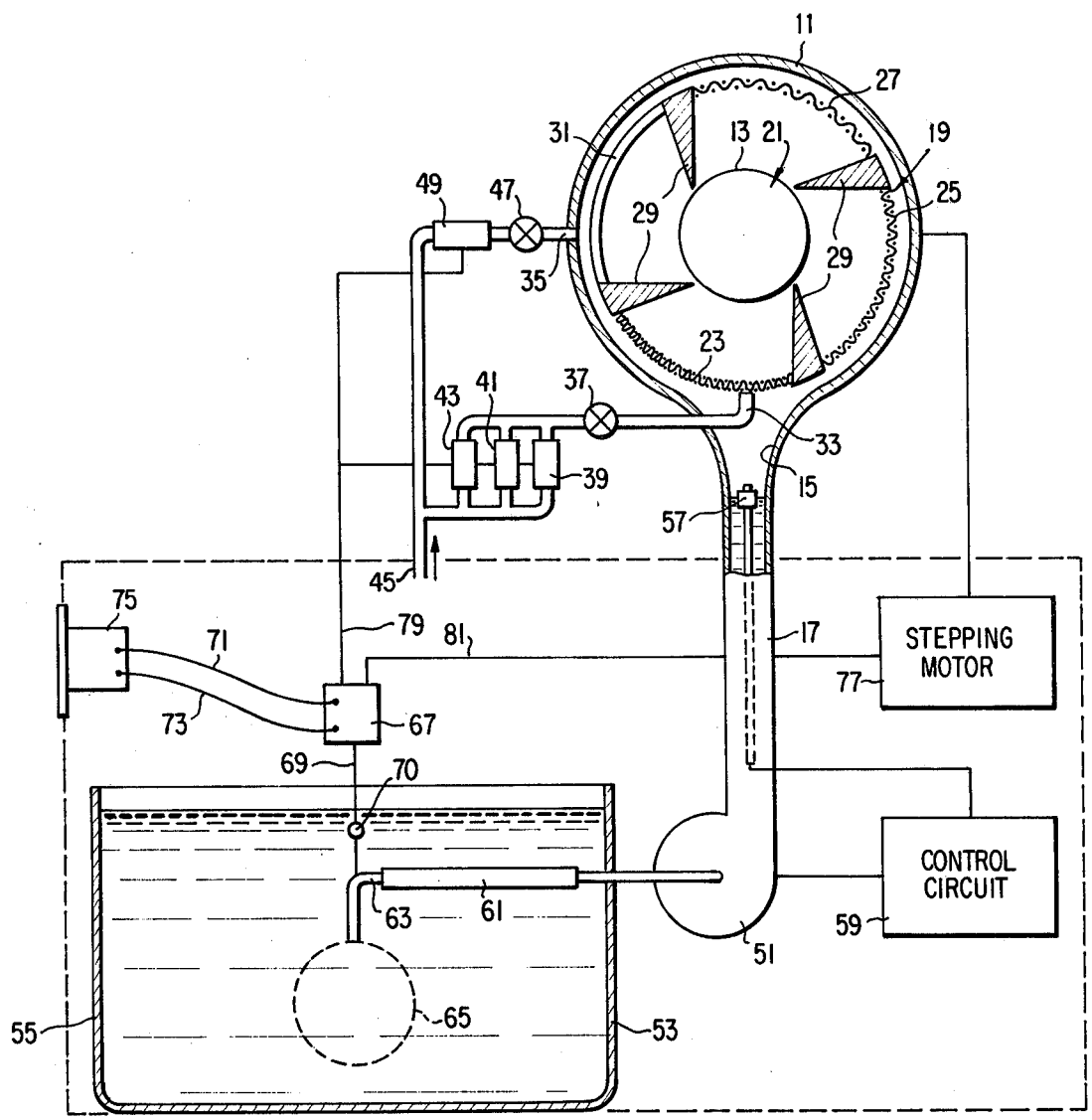

METHOD AND APPARATUS FOR AUTOMATICALLY FRACTIONATING A SAMPLE OF PARTICULATE MATERIAL INTO DISCRETE SIZE FRACTIONS

CROSS-REFERENCE TO RELATED APPLICATION

The present Application is an improvement over the invention disclosed in U.S. Pat. No. 3,943,754 issued Mar. 16, 1976.

BACKGROUND OF THE INVENTION

1. Field of the Invention

The present invention relates to the measurement of the relative weight proportions of different size fractions of a sample of particulate material.

2. Description of the Prior Art

Measurement of the size of particles in a particulate mass is required in a great many industrial operations. Much of this particle sizing is now accomplished manually by having a technician expose samples of the powder to a series of sieves — pans with woven wire bottoms — from which, by weighing the amounts passing and retained, he can calculate percentages of particles having certain sizes. Numerous difficulties are encountered, however with sieving as now practiced. Sieves, especially the finer meshes, are fragile. If misused, their openings are likely to be distorted, greatly biasing subsequent results obtained with them. Sieve openings very readily become blocked with irregularly shaped particles of near opening size, if too much force is exerted in trying to cause them to pass. Then the sieve has to be cleaned carefully, or again its openings will be disturbed. The weight of powder passing and retained must separately be obtained which leads to the possibility of errors in recording weights or manipulating the powder fractions. Also, the operator must determine when all the powder that can pass a sieve has done so. This, being often a judgement decision, leads to non-reproducibility. Finally, dry sieving is frequently utilized simply because it eliminates the drying of fractions even though wet sieving gives better particle dispersion, and hence, more representative results.

My previous patent describes a method and apparatus for determining the relative weight proportions of different size fractions of the sample of particulate material. However, my previously described apparatus is manually operated creating a need for an improved method and apparatus for fractionating a sample of particulate material into discrete size fractions.

SUMMARY OF THE INVENTION

Accordingly, one object of the present invention is to provide an improved method and apparatus for determining the relative weight proportions of different size fractions of the sample of particulate material.

It is another object of the present invention to provide such a method and apparatus wherein the user need only introduce the sample and later automatically recover a readout of the results.

The objects of the present invention are achieved by apparatus for automatically determining the relative weight proportions of differently-sized fractions of the sample of particulate material. The apparatus includes a casing having an inlet opening at a middle region thereof and a discharge outlet at a lower region thereof. Rotatably mounted within the casing is a tumbler having at least one screen member and one open space around its periphery bordered by inwardly extending dividers. The dividers divide the interior of the tumbler into a plurality of compartments, each of which leads from the inlet opening to the discharge outlet when the respective screen member or the open space is aligned with the discharge outlet. The apparatus further includes at least one spray nozzle disposed adjacent the periphery of the tumbler to selectively introduce fluid into the compartments to selectively discharge particulate material retained therein, a closed porous member for sequentially accumulating particulate material discharged from the several compartments, and a device for weighing the contents of the closed porous member.

Another aspect of the present invention involves a method of determining the relative weight proportions of differently sized fractions of the sample of particulate material. The method includes the steps of providing a rotatable tumbler having at least one screen member and one open space around its periphery bordered by inwardly extending dividers for dividing the interior of the tumbler into a plurality of compartments, rotating the tumbler until the compartment corresponding to the one screen member or the open space is lowermost, charging a sample of particulate material into the compartment, and causing a first fraction of the sample to pass out of the compartment. The method further includes the steps of entraining the first fraction of particulate material in a moving body of fluid, passing it through a porous weighing member, and measuring the weight of the first fraction of particulate material deposited on the porous weighing member. The method further includes the steps of rotating the tumbler until the next compartment is lowermost, and repeating the process until all fractions have been accumulated in the weighing member.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

The FIGURE is a schematic diagram of the preferred embodiment of the apparatus for determining the relative weight proportions of differently sized fractions of a sample of particulate material of the invention.

DESCRIPTION OF THE PREFERRED EMBODIMENT

Referring now to the drawing, there is shown a schematic diagram of the apparatus of the present invention. As shown, the apparatus includes a stationary cylindrical casing 11 having its axis disposed to the horizontal. The casing has front and rear end portions, and the front end portion is provided with a centrally located inlet opening 13. At the lower end of the casing in the side wall thereof, there is provided a discharge outlet 15 which communicates with a standpipe 17. Coaxially disposed within the casing is a tumbler 19 for receiving the particulate material. The tumbler is rotatably mounted in suitable journal bearings by means of a shaft extending from its rear end portion. The front end portion of the tumbler is provided with a centrally located access opening 21 which is in register with the inlet opening 13 in the front end portion of the casing 11. Screen members 23, 25, and 27, having different size openings to permit the passage of smaller particles but the rejection of larger ones are arranged in order of increasing opening size around the periphery of the tumbler 19 in the clockwise direction. Axially spaced longitudinal dividers 29 separate the screen members. The last space in the sequence 31 is left entirely open instead of being fitted with a screen. The dividers 29 extend inwardly generally toward the center of the tumbler 19 and link the front and rear end portions thereof. The dividers 29 separate the interior of the tumbler 19 into a plurality of compartments, each compartment leading from the inlet opening 13 to the discharge outlet 15 when the respective screen member is aligned with the discharge outlet.

Two sets of spray nozzles are disposed at the periphery of the tumbler: one 33 at the tumbler's lowermost point, and the other 35 at a point displaced 90° therefrom in the clockwise direction. The lower set of spray nozzles 33 is connected through the manual valve 37 and the solenoid valves 39, 41 and 43 to the common liquid inlet line 45 to which the upper set of spray nozzles 35 is also connected through the manual valve 47 and the solenoid valve 49.

The standpipe 17 connected to the discharge outlet 15 of the casing 11 projects downwardly to a suitable pump 51, such as a centrifugal pump, for supplying the discharged particulate material under pressure to a body of liquid contained within a suitable tank 53. A float switch 57 disposed in the liquid in the standpipe 17 is connected to a conventional control circuit 59 for slowing the speed of the pump 51 in response to fall of the float switch with liquid level to maintain the level of liquid in the standpipe constant. A flexible member 61 connects the pump 51 to an L-shaped inlet tube 63 of a porous material-retaining member 65. Associated with the member is a weighing device 67 which includes a mechanical transducer link 69 pivotally connected as at 70 to the tube 63. The weighing device itself includes an electrical transducer and a conventional microprocessor connected by suitable wires 71 and 73 to a readout device 75 for computing and displaying the relative weight proportion of the material contained within the porous pocket or material-retaining member 65. As will be presently apparent, it is advantageous to have the transducer calibrated such that the tare weight imposed upon the transducer of the weighing device 67 through the mechanical link 69 due to the weight of the member 65 and effect of the flexible member 61 is compensated for so that the readout is 0 when member 65 is empty of material.

To complete the structural assembly as shown in the FIGURE, there is provided a suitable drive device such as an electric stepping motor 77 to oscillate or to rotate the tumbler 19.

The microprocessor utilizes a stored program to sequence the machine action (operation of the valves and the stepping motor over connections shown as leads 79 and 81) and to perform data collection, computation and presentation.

To utilize the assembly as illustrated in the FIGURE, the screen member 23 having the smallest openings is positioned over the discharge outlet 15. Next, a sample mass of particulate material having varying sizes is charged into the lowermost compartment through the access opening 21 in the tumbler 19 to rest upon the screen member 23. Valve 49 is closed whereas the valves 37, 39, 41 and 43 are open to create an upward spray of water or other conveying liquid from the nozzles 33 into the lowermost compartment. At the same time, the motor 77 is caused to oscillate the tumbler 19 so that the spray alternately projects against and through all elements of the screen member 23. The velocity of the spray is selected by manual valve 37 such that the particle mass directly in its path is lifted without being carried above the dividers 29 separating one screen size from another. The particles drop back on the screen member 23 once they are out of the direct path of the spray. The oscillation of the screen member 23 also causes the particles alternately to shift from one side of the compartment to the other. The combined lifting and dropping of the particles on the screen member and the rolling and sliding of the particles across the screen member provides multiple opportunities for all particles smaller than the openings in the screen member to pass therethrough. These particles are discharged through the outlet 15 into the stand-pipe 17 and pass through the flexible line 61 and into the interior of the material retaining member 65 wherein they are trapped. As noted previously, the member 65 is porous so that the liquid can pass freely therethrough but the particulate material is retained therein.

In the meantime, the control circuit 59 regulates the speed of the pump 51 to prevent introduction of air into the material retaining member 65 which could distort the weighing operation. The standpipe 17 permits entrapped bubbles of air to escape while ensuring that the pump 51 itself never draws in air directly.

When the accumulation of particles substantially ceases as detected by the weighing device 67, all of the particles able to pass through the finest screen member 23 will have passed into and been retained within the material retaining member 65.

The motor 77 is now caused to rotate the tumbler 19 by 90° in the clockwise direction so that the screen member 25 with the next largest openings is lowermost. This shift in relative position also brings the finest screen member 23 with its load of retained particles into juxtaposition with the other set of spray nozzles 35. Valve 49 is opened to create a laterally directed spray into the adjacent compartment. The velocity of this spray is adjusted by manual valve 47. It should be understood that manual valves 37 and 47 are adjusted once for each variety of particulate material and will not ordinarily require further adjustment until another variety of particulate material is used. At the same time, the oscillatory motion of the tumbler 19 is resumed with an amplitude bringing all elements of the lowermost screen member 25 across the spray projected from the lower set of spray nozzles 33. Liquid emerging from the set of spray nozzles 35 causes the previously retained particles to be lifted from the finer screen member 23 across the divider 29 and dropped onto the screen member 25 having the next largest openings. Valve 39 is closed to lessen the discharge from the lower set of nozzles 33 since the openings in the screen member 25 are larger and thus less restrictive of flow and it is desired to keep the velocity of the spray such that the particle mass directly in its path is lifted without being carried over the divider 29. It may be noted again that the manual valves 37 and 47 permit fine adjustment of either spray if overflow of liquid into another compartment appears likely. Particles which are of the next smallest particle size such as to pass the second screen member 25 are ultimately passed therethrough under the combined lifting and rolling action produced by the spray from the lower set of nozzles 33 and the oscillatory movement of the tumbler 19. The passing particles are, as before, trapped in the material retaining member 65 downstream and their cumulative weight is detected.

When further weight change ceases, the motor 77 is caused to rotate the tumbler 19 through another 90° in the clockwise direction so that the screen member 27 with still larger openings is lowermost. The laterally directed spray through the set of nozzles 35 into the adjacent compartment and the oscillatory motion of the tumbler 19 again remove and wash the retained particles into the new lowermost screen member 27. Valves 39 and 41 are closed to lessen the discharge from the lower set of nozzles 33. As before, particles of size such as to pass the screen member are discharged through the discharge outlet 15, entrained in liquid, collected in the interior of the material retaining member 65 and their cumulative weight detected.

Finally, the motor 77 is caused to rotate the tumbler 19 another 90° in the clockwise direction so that the section 31 without a screen member is aligned with the discharge outlet 15. The action of the set of nozzles 35 and the oscillatory motion of the tumbler 19 again dislodge and drop all remaining particles through the open space 31 to be collected in the interior of material retaining member 65. When the accumulation ceases all of the particles will have passed into and been retained in the member 65. At this point, completion of a test cycle is indicated and the relative weight proportion of each size fraction is computed and displayed.

It will be apparent that the relative weights of all of the fractions of various sizes of particulate material can be obtained in this way. Exact weights are not obtained since the buoyancy of the liquid is not taken into account. Relative weights, however, are sufficient for calculating the percentages of mass represented by the several fractions. Mass percentages are the information desired in particle size analysis. It should be noted that successive sample batches can be processed without cleaning out the tumbler since screen cleaning for further use is achieved automatically by the passing of the screen members across the liquid spray as the tumbler is rotated.

Obviously, numerous modifications and variations of the present invention are possible in light of the above teachings. The preferred embodiment has been directed to a fractionating system with three screens and one blank position. Clearly, a system could have only one screen or many screens, a practical upper limit probably being 8 or 10. The screens also are shown as being curved to fit the periphery of the tumbler. It will be apparent that the screens could be flat, thereby simplifying the mounting problem. If as many as 8 or 10 flat segments were used, the nozzles could be rigidly mounted, as described above. However, if only 3 flat screens and one free space were used, it might be necessary to mount the nozzles on arms following the contour of the tumbler to prevent the nozzles from being disposed too far from the screens during portions of each test cycle. It is therefore to be understood that within the scope of the claims, the invention may be practiced otherwise than as specifically described.

What is claimed as new and desired to be secured by Letters Patent of the United States is:

1. Apparatus for automatically determining the relative weight proportions of differently sized fractions of a sample of particulate material, comprising:
   a casing having an inlet opening at an upper region thereof and a discharge outlet at a lower region thereof;
   a tumbler rotatably mounted within the casing, the tumbler having at least one screen member and one open space around its periphery bordered by inwardly extending dividers for dividing the interior of the tumbler into a plurality of compartments, each compartment leading from the inlet opening into the discharge outlet when the respective screen member is aligned with the discharge outlet;
   means for selectively introducing fluid into the compartments to selectively discharge particulate material retained in the compartments;
   means for sequentially accumulating particulate material discharged from the several compartments; and
   means for weighing the contents of the accumulating means.

2. The apparatus recited in claim 1 including:
   motor means for rotating the tumbler.

3. The apparatus recited in claim 1 wherein:
   the fluid introducing means comprises at least one spray nozzle disposed adjacent the periphery of the tumbler.

4. The apparatus recited in claim 1 wherein:
   the accumulating means is a closed porous member.

5. A method of determining the relative weight proportions of differently sized fractions of a sample of particulate material comprising the steps of:
   a. providing a rotatable tumbler having at least one screen member around its periphery and one open space bordered by inwardly extending dividers for dividing the interior of the tumbler into a plurality of compartments;
   b. rotating the tumbler until the compartment corresponding to the one screen member is lowermost;
   c. charging a sample of particulate material into the lowermost compartment of the tumbler;
   d. causing a first fraction of the sample of particulate material to pass out of the lowermost compartment of the tumbler;
   e. entraining the first fraction of particulate material in a moving body of fluid and passing the fluid through a porous weighing member;
   f. measuring the weight of the first fraction of particulate material disposed on the porous weighing member;
   g. rotating the tumbler until the next compartment is lowermost; and
   h. repeating steps (c)–(f) for at least one other fraction.

6. The method recited in claim 5 wherein step (d) comprises the steps of:
   projecting a spray of fluid into the lowermost compartment of the tumbler; and
   oscillating the tumbler about its rotation axis.

* * * * *